US00PP15850P2

(12) United States Plant Patent
Yanny

(10) Patent No.: US PP15,850 P2
(45) Date of Patent: Jul. 12, 2005

(54) *THUJA* PLANT NAMED 'BAIL JOHN'

(50) Latin Name: *Thuja occidentalis*
Varietal Denomination: Bail John

(75) Inventor: Michael D. Yanny, Milwaukee, WI (US)

(73) Assignees: Johnson's Nursery, Inc., Menomonee Falls, WI (US); Bailey Nurseries, Inc., Newport, MN (US)

( * ) Notice: Subject to any disclaimer, the term of this patent is extended or adjusted under 35 U.S.C. 154(b) by 112 days.

(21) Appl. No.: 10/774,991

(22) Filed: Feb. 9, 2004

(51) Int. Cl.[7] ..... A01H 7/00
(52) U.S. Cl. ..... Plt./213
(58) Field of Search ..... Plt./213

*Primary Examiner*—Kent Bell
*Assistant Examiner*—Louanne Krawczewicz Myers
(74) *Attorney, Agent, or Firm*—Penny J. Aguirre

(57) ABSTRACT

A new cultivar of *Thuja occidentalis* 'Bail John' characterized by its compact, broadly pyramidal plant habit and its densely packed dark green foliage that has good color retention and resistance to burning in winter.

2 Drawing Sheets

Botanical classification: *Thuja occidentalis.*
Varietal denomination: 'Bail John'.

BACKGROUND OF THE INVENTION

The present invention relates to a new and distinct cultivar of *Thuja occidentalis* and will be referred to hereafter by its cultivar name, 'Bail John'. 'Bail John' represents a new Arborvitae, an evergreen tree grown for landscape use.

The inventor discovered this new Arborvitae as a single plant in a nursery block of *Thuja occidentalis* 'Techny' (un-patented) in the summer of 1989. The inventor selected the new cultivar as unique because the foliage appeared to be noticeably denser, resulting in a more compact plant with a broader plant habit than 'Techny'. 'Bail John' is a naturally occurring branch sport of 'Techny', as all plants in the block from which it was selected were derived from cuttings of 'Techny'. Further testing revealed that 'Bail John' did not require the repeated shearing that is required with 'Techny' to produce a marketable, dense plant. 'Bail John' is similar to its parent, 'Techny', in that it has the same very dark green foliage that is retained throughout the winter.

Although other cultivars of *Thuja occidentalis* are known to the inventor that are compact, they are considerably more dwarf, differ in plant shape or lack the foliage characteristics of 'Bail John' derived from 'Techny'. In comparison to *Thuja occidentalis* 'Holmstrup', (un-patented) 'Bail John' is less pyramidal in shape, has greater winter hardiness, and has darker foliage with better color retention in the winter months.

Asexual reproduction of the new cultivar was first accomplished by hardwood cuttings in Menomonee Falls, Wis. in summer of 1989 by the inventor. Further generations of cuttings were taken in following years and trials have determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Bail John', as unique from all other selections and forms of *Thuja occidentalis* known to the inventor.

1. Exhibits a compact, broadly pyramidal growth habit.
2. Forms dense foliage that requires less shearing than its parent, 'Techny'. The denser foliage results both from the existence of fuller sprays with a greater number of branchlets per spray and from shorter internodes between the sprays and branchlets.
3. A 14 year-old plant obtains a height of about 1.8 m (6 ft) and a width of about 1.2 m (4 ft) with only 6 shearings during the 14 year period; 'Techny', when subjected to the same amount of shearing reaches a height of about 3.2 m (10.5 ft) and a spread of about 1.7 m (5.5 ft). Plants of 'Bail John' that were grown for 6 years without shearing attained a height of about 1.2 m (4 ft) and a spread of about 76 cm (2.5 ft); plants of 'Techny' grown under the same conditions attained a height of about 1.8 m (6 ft) and a spread of about 1.1 m (3.5 ft).
4. Exhibits the same dark green foliage that is characteristic of 'Techny' with foliage color retention during the winter months and resistance to winter burn.
5. Exhibits winter hardy to at least U.S.D.A. Zone 4.

BRIEF DESCRIPTION OF THE DRAWING

The plants in the accompanied photographs were grown outdoors in Menomonee Falls, Wis. from rooted hardwood cuttings.

FIG. 1 is a digital photograph of a six year-old plant of 'Bail John' grown without shearing for six years and illustrates the growth habit, foliage characteristics, and height and spread.

FIG. 2 is a digital photograph comparing 14 year-old plants of 'Bail John' (right) and 'Techny' (left) that have been subjected to the same amount of shearing 6 times during the 14 years. The plants in the background of FIG. 2 are 14 year-old plants of *Thuja occidentalis* 'Pryamidalis' (unpatented).

FIG. 3 is a digital photograph of a comparison of sprays of foliage taken from 4 year-old plants of 'Bail John' (right) and 'Techny' (left).

The colors in the photographs are as close as possible with the photographic and printing technology utilized. The color values cited in the detailed botanical description accurately describe the colors of the new *Thuja*.

DETAILED BOTANICAL DESCRIPTION

The following is a detailed description of the new cultivar. General information is provided from data collected on plants grown for up to 14 years as grown outdoors in a trial field in Menomonee Falls, Wis. The detailed botanical data was taken from four year-old plants grown in five-gallon containers in St. Paul, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Bail John' is a cultivar of *Thuja occidentalis*.

Parentage: Naturally occurring branch sport of *Thuja occidentalis* 'Techny' (un-patented).

General description:

*Plant type.*—Coniferous, evergreen, monoecious tree for landscape use.

*Growth habit.*—Broadly pyramidal with dense foliage. The requirement for shearing to maintain a dense habit is reduced in comparison to 'Techny'.

*Height and spread.*—A 14 year-old plant obtains a height of about 1.8 m (6 ft) and a width of about 1.2 m (4 ft) with only 6 shearings during the 14 year period; 'Techny', when subjected to the same amount of shearing reaches a height of about 3.2 m (10.5 ft) and a spread of about 1.7 m (5.5 ft). Plants of 'Bail John' that were grown for 6 years without shearing attained a height of about 1.2 m (4 ft) and a spread of about 76 cm (2.5 ft); plants of 'Techny' grown under the same conditions attained a height of about 1.8 m (6 ft) and a spread of about 1.1 m (3.5 ft). The maximum height and spread of 'Bail John' has not been determined.

*Cone development.*—Male and female cones arise from terminals of branchlets in August and persist for several months. Cones are sparse in quantity and are infrequent on young plants.

*Hardiness.*—At least Zone 4, 'Bail John' has not been tested in colder zones, the parent plant, 'Techny' is hardy in Zones 2 to 8.

*Culture.*—Grows best in deep, moist, well-drained soils in full sun.

*Diseases and pests.*—No susceptibility or resistance to diseases or pests known to affect *Thuja* has been observed for 'Bail John'.

*Root description.*—Fibrous.

Growth and propagation:

*Propagation protocol.*—Harwood cuttings, 5 to 20 cm in length with about 5 cm of 2 year old wood at the base, are taken in mid-March and placed in opaque plastic bags with little or no moisture added. The bags of cuttings are kept in an unheated building, out of sunlight until early to mid May. In May, the cuttings are stripped at the base 5 to 7.5 cm and quick dipped in 1600 ppm IBA and 800 ppm NAA. Cuttings are stuck in coarse sand, outdoors, under natural light without shading, under mist for 10 seconds every 4 minutes during the daylight hours.

*Time required for root initiation.*—6 to 7 weeks in mid summer.

*Time required for root development.*—Rooted cuttings fully develop in one-quart containers in about one year; plants are about 20 to 30 cm in height. Field growing of the one-quart containers for three years without shearing develop into plants 0.9 m in height (3 ft) and about 76 cm in spread (2.5 ft).

Stem description:

*Shape.*—Twigs are flattened, more mature branches are round and knobby.

*Stem color.*—New growth on sprays (twigs) are 144A (yellow-green), young branches N199C (grey-brown), branches mature to 201B (grey) with brown markings and shadings of N199B and 199C.

*Stem size.*—Main branches: about 0.7 to 2 cm in diameter, branch length is approximately equivalent to height of plant, secondary branches: about 0.5 to 2 cm in diameter, up to about 30 cm in length.

*Stem surface.*—Twigs are scaly, young branches are glabrous and knobby, mature bark is thin, fibrous, fissured into connecting ridges.

*Branching.*—Multiple main branches arise from base (about 4 to 6), secondary branches (about 2 to 4) emerge per main branch, numerous small sprays emerge from secondary branches. 'Techny' has less secondary branching.

*Branch aspect.*—Main stems upright, secondary stems more outward with sprays that curve upwards.

*Internode length.*—Between main and secondary stems: about 0.5 to 2 cm, between sprays: about 0.5 to 2 cm, between branchlets: about 0.25 to 1 cm. 'Techny' has longer internodes between sprays, typically 2 to 4 cm and longer internodes between branchlets, typically 1 to 1.5 cm.

Foliage description:

*Leaf arrangement.*—Numerous leaves arranged on flat branchlets (may be alternate or opposite), leaves are born in 2 ranks of opposite pairs (4-ranked), scale-like, densely imbricate.

*Leaf shape.*—Side pair keeled, flat pair flattened and fanlike (narrowly wedge to diamond shaped).

*Leaf division.*—Simple.

*Leaf base.*—Cordate.

*Leaf apex.*—Acute.

*Leaf venation.*—Not visible.

*Leaf margins.*—Entire.

*Leaf surface.*—Upper and lower; glabrous, slightly glaucous.

*Leaf color.*—Young upper surface: 137A, young lower surface: 137D. Mature upper surface: 137A, mature lower surface: 137B. Mature leaf color is retained in winter months.

*Resin glands.*—Conspicuous, present on the center leaves of branchlets and side shoots off branchlets, 0.5 mm wide and 0.75 mm in length, 146 D to 146C in color on mature leaves.

*Leaf size.*—2 mm in length, 2 mm in width.

*Spray and branchlet size.*—Sprays: about 22 cm in length, 18 cm in width, branchlets: about 11 to 15 cm in length, 4 to 6 cm in width.

*Leaf quantity.*—About 200 to 300 leaves per branchlet, about 8 to 12 branchlets per spray.

*Foliage fragrance.*—Acrid (tansy-like) when foliage is crushed.

Cone description:

*General occurrence.*—Monoecious, both female and male cones arise on terminal region of branchlets in late summer, sparse in quantity and infrequently on young plants.

*Female cone description.*—Composed of 6 pairs of scales, ovoid in shape, about 1 to 4 mm in length and 0.5 to 3 mm in width, color between 144B and 144C when newly formed and matures at dehiscence to 165A, inner scales are fertile with 2 ovules.

*Male cone description.*—Born on terminals of leaves, composed of scales, globose in shape, 1.5 mm in diameter, color 144B when newly formed turning 165A at maturity, 6 stamens in 3 pairs, anthers 12C in color, pollen not visible.

*Lastingness of cones.*—2 to 4 months.

*Number of cones.*—Highly variable, 3 to 4 female cones and 4 to 5 male cones is typical per spray if present.

*Seeds description.*—Winged, papery, 164B in color, about 6 to 8 per scale, about 5 mm in length and 3 mm in width.

It is claimed:

1. A new and distinct cultivar of *Thuja* plant named 'Bail John' as herein illustrated and described.

* * * * *

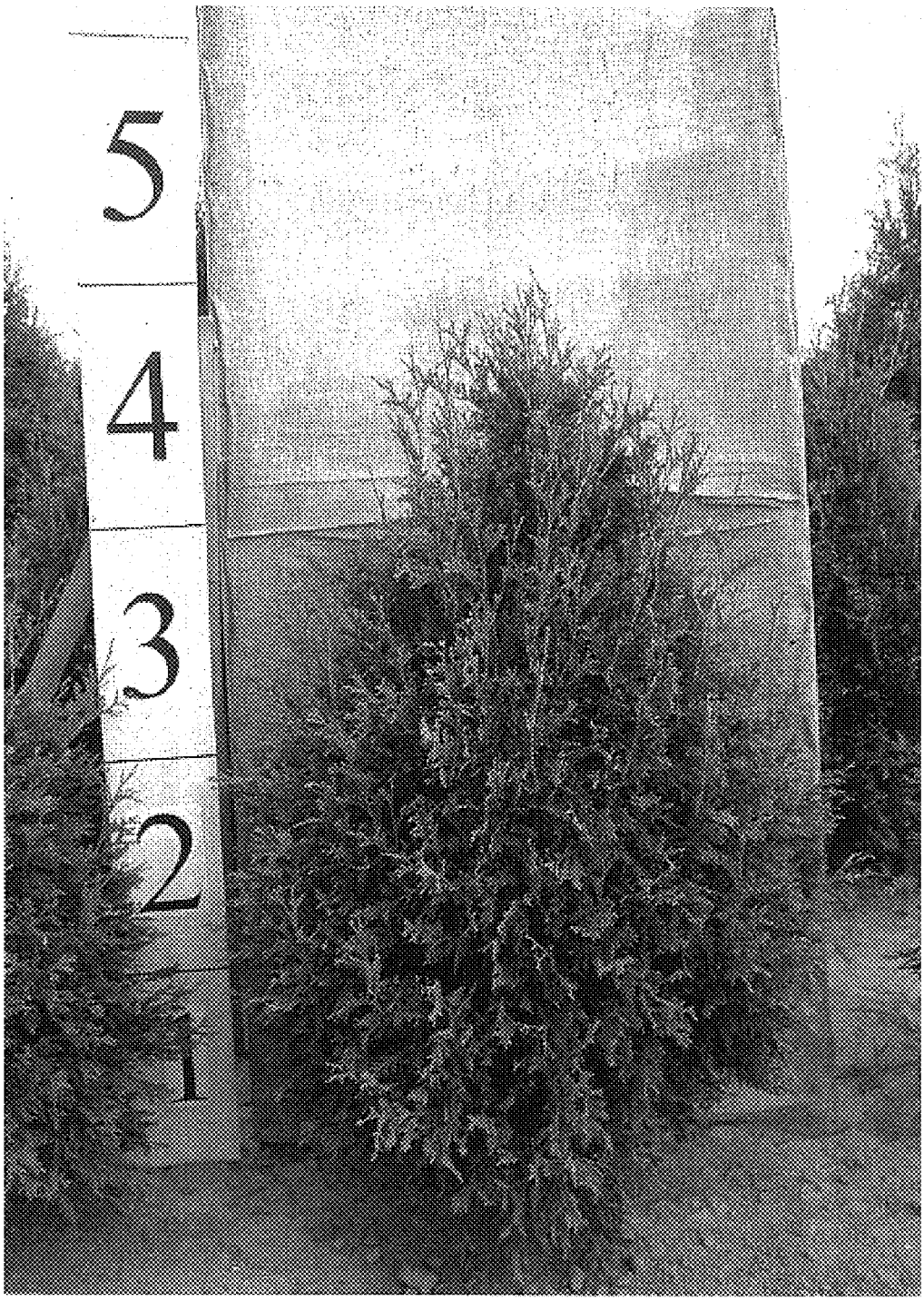
Figure One

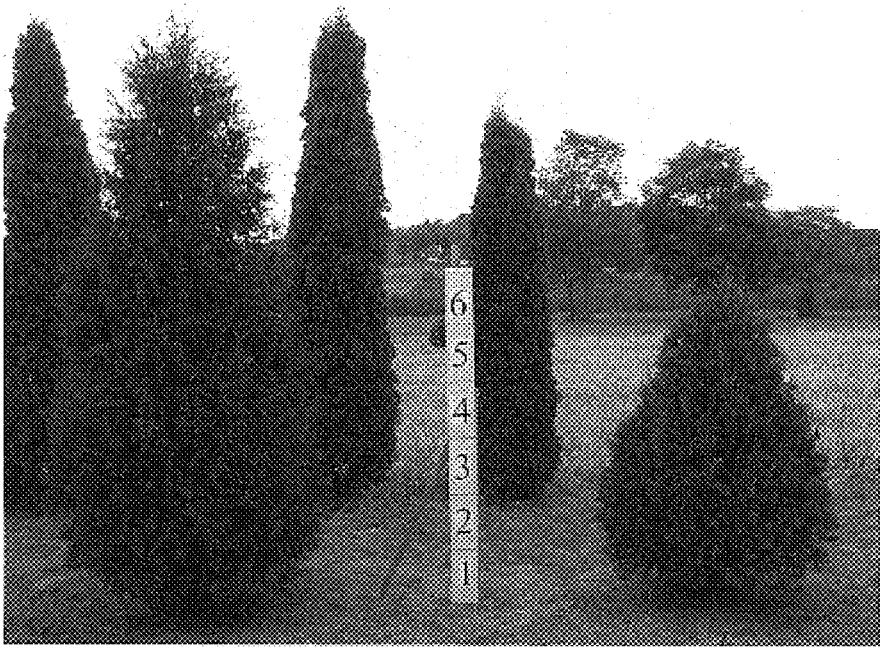
Figure Two
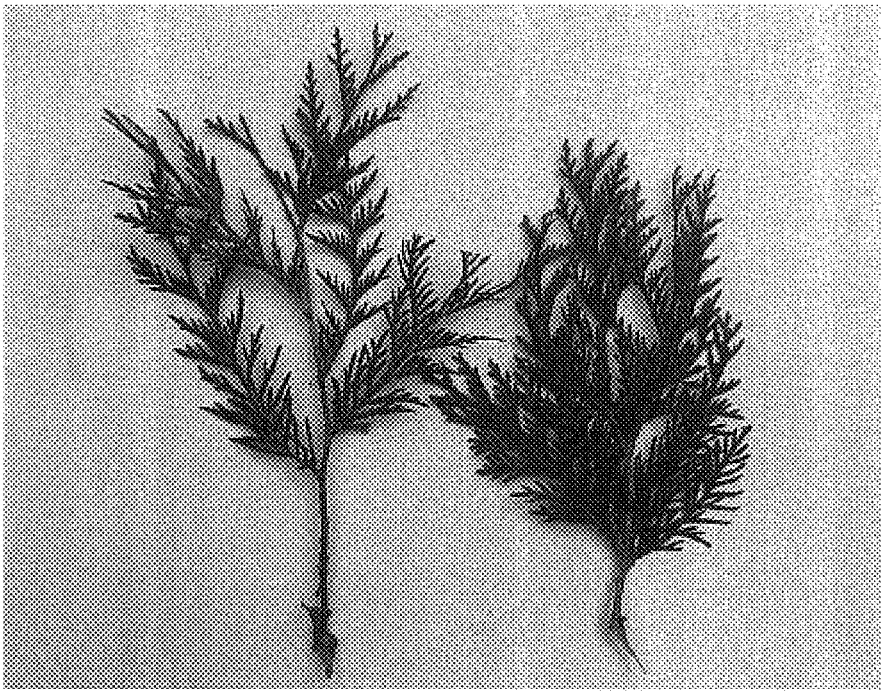
Figure Three